United States Patent [19]

Lindstroem et al.

[11] 4,108,426
[45] Aug. 22, 1978

[54] DEVICE FOR HOLDING THE HEAD OF A PATIENT

[75] Inventors: Harry Lindstroem, Solna; Sverre Kvaerna, Farsta, both of Sweden

[73] Assignee: Siemens Aktiengesellschaft, Berlin & Munich, Fed. Rep. of Germany

[21] Appl. No.: 872,448

[22] Filed: Jan. 26, 1978

[51] Int. Cl.² ............................................. A61G 13/00
[52] U.S. Cl. .................................................. 269/328
[58] Field of Search ................... 269/328, 71, 75, 246, 269/258

[56] References Cited

U.S. PATENT DOCUMENTS

| 2,966,383 | 12/1960 | Boetcker et al. | 269/328 |
| 3,835,861 | 9/1974 | Kees et al. | 269/328 |

Primary Examiner—Robert C. Watson
Attorney, Agent, or Firm—Hill, Gross, Simpson, Van Santen, Steadman, Chiara & Simpson

[57] ABSTRACT

A device for holding the head of a patient in a fixed position during a surgical operation characterized by a base support, a ring-like curved element having a sufficient radius of curvature to enable receiving the head of a patient within the element, means for supporting the ring-like element on the base support including a ball and socket joint having means for manually arresting the joint in any desired position, a pad supported on a rod acting as a headrest, a pin supported on a rod for holding the head in a fixed position on the pads, and means for mounting the rods supporting the pad and the rod for supporting the pins so that a head is clamped therebetween within the curved element. Preferably, the curved element is a ring having an opening along one side and the mounting means for each of the rods includes a bolt extending through spaced apertures in the ring so that the position of the rods can be adjusted on the ring. In addition, the supporting means for the ring preferably includes a clamp which enables displacement of the ring or curved element within the clamp to vary the position of the opening relative to the supporting means.

10 Claims, 3 Drawing Figures

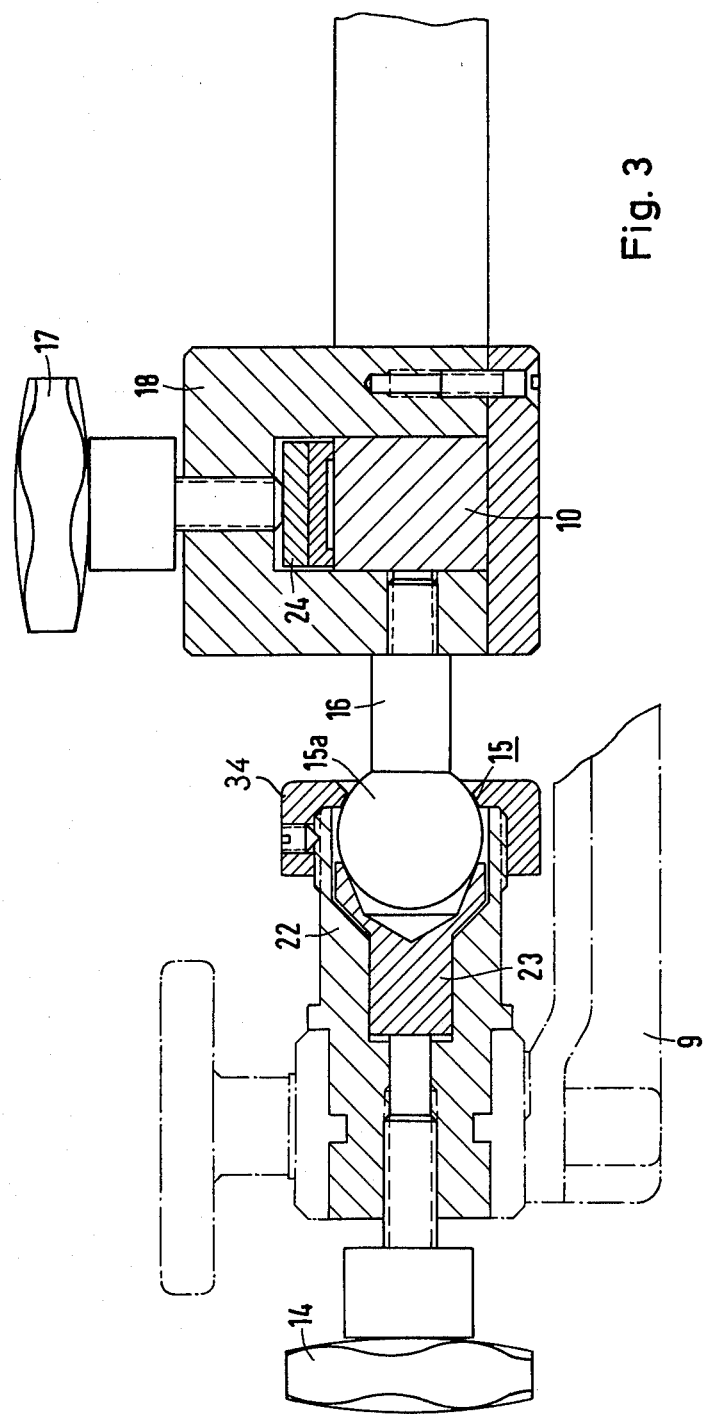

DEVICE FOR HOLDING THE HEAD OF A PATIENT

BACKGROUND OF THE INVENTION

1. Field of the Invention

The present invention is directed to a device for holding or clamping the head of a patient in a fixed position during a surgical operation which device includes a base support, a ring-like curved element secured on the support for encircling the head of a patient with the element adjustably supporting pads serving as a headrest and a pin for holding the head in a fixed position on the pads.

2. Prior Art

In the case of surgery for example a neurosurgical operation, it is necessary that the head of the patient be fixed or locked in a given position and that the operating field will be readily accessible to the physician. An example of a neutrosurgical headrest is disclosed in a brochure of the Mayfield Company entitled "Neurosurgical Headrest". In the brochure, a device is shown wherein the head is secured at three points in a clamp. A disadvantage with this device is that the adjustment possibilities of the clamp in relation to the head are limited. Moreover, it is not possible to simultaneously employ pads and pins in the device of the brochure.

Another type of holding device for the head of a patient such as during irradiation is disclosed in the brochure of the Studsvik AB Atomenergi, Sweden entitled "Applikator Fur Hypophysendestrucktion". The disadvantage of this device consists in that the ring is rigidly mounted to a patient supporting device which means that the ring of the fixation or holding arrangement is only adjustable in relation to the head of the patient by rotation of the ring on its axis.

SUMMARY OF THE INVENTION

The present invention is directed to a device which was a curved element for holding the head of a patient in a fixed position during a surgical operation which device permits a multi-lateral orientation or alignment of the curved element in relation to the head of the patient.

To accomplish this task, the device for holding the head of the patient in a fixed position during a surgical operation comprises a base support, a ring-like curved element having a sufficient radius of curvature to enable receiving the head of a patient within the element, means for supporting a ring-like curved element on the base support including a ball and socket joint having means for manually arresting the joint in any desired position, a pad supported on a rod acting as a headrest, a pin supported on the rod for holding the head in a fixed position on the pad, means for mounting the rod supporting said pad on the element and means for mounting the rod supporting the pin on the element, both of said means for mounting being adjustable to enable changing the length of the respective rods extending from the element to clamp the head of the patient between the pad and the pin. By the use of the ball and socket joint, the curved element which may be a complete ring or a partial ring can be adjusted in all directions in relation to the head of the patient.

Another advantage of the preferred embodiment in which the ring is partially opened is that the area of the head of the patient which is to undergo operation can be positioned in the open space of the ring so that it is more freely accessible during the operation.

BRIEF DESCRIPTION OF THE DRAWINGS

FIG. 3 is a cross-sectional view taken along lines III—III of FIG. 2.

DESCRIPTION OF THE PREFERRED EMBODIMENTS

Figure 1:
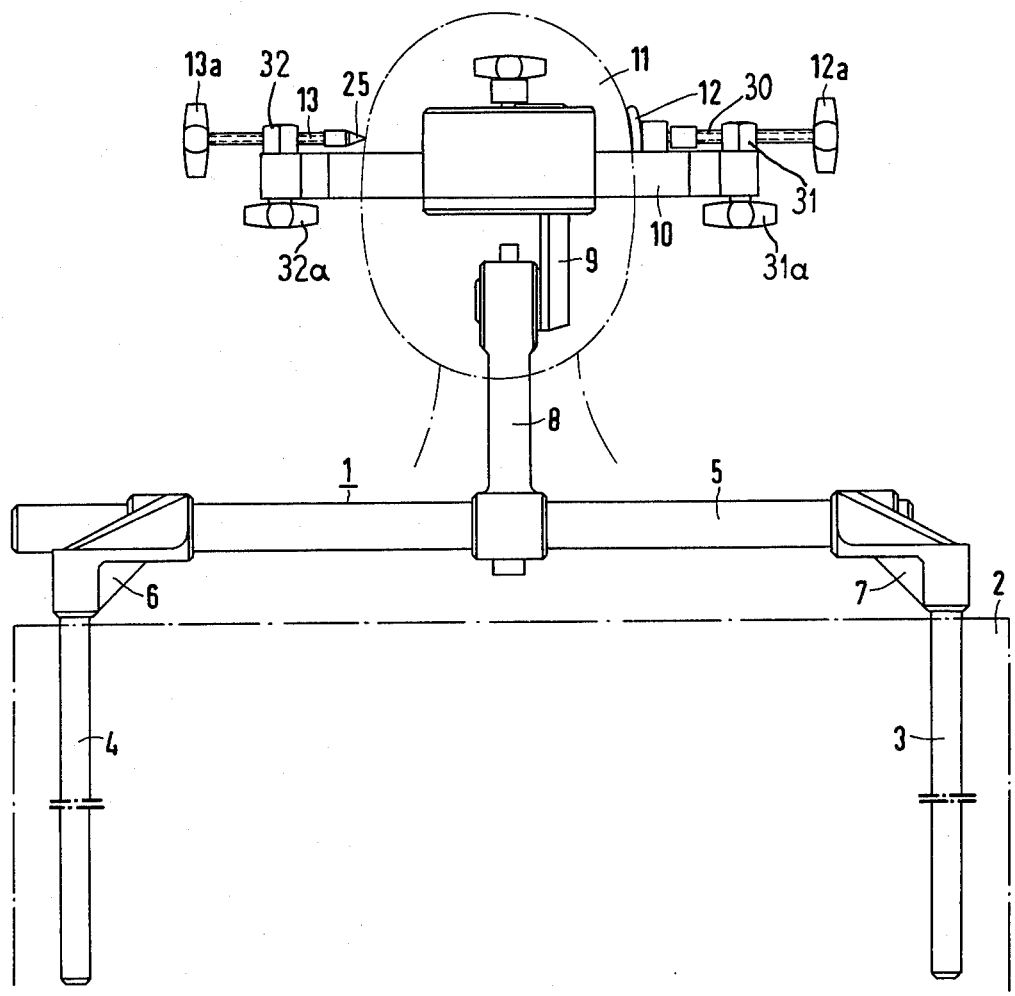
FIG. 1 is an end view of the device in accordance to the present invention.
Figure 2:
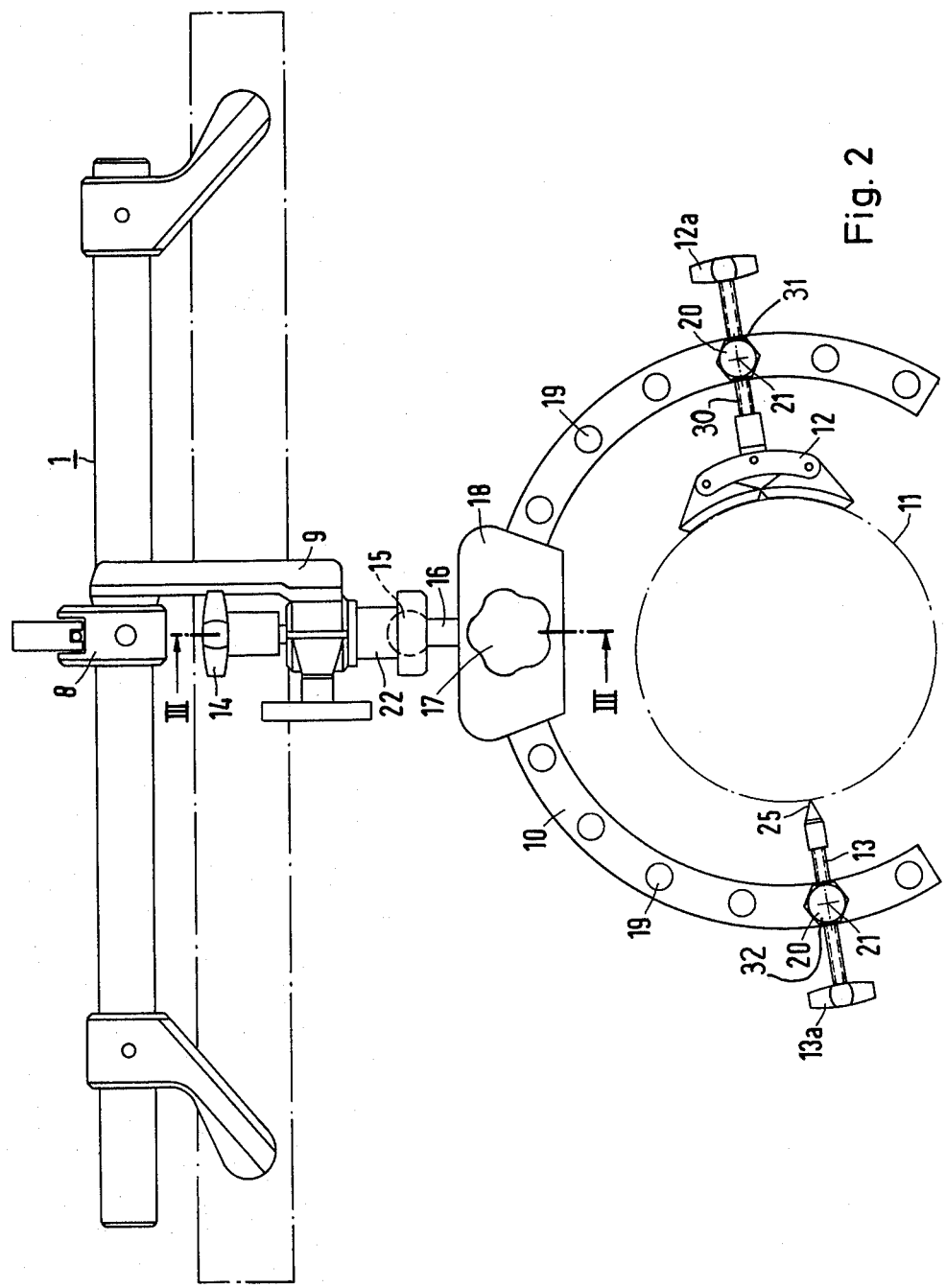
FIG. 2 is a plan view of the device of FIG. 1.

The principles of the present invention are particularly useful when incorporated in a device 1 illustrated in FIGS. 1 and 2 for holding the head 11 of a patient in a fixed position such as during a surgical operation.

As illustrated in FIG. 1 the device 1 is mounted or secured on a support 2, such as a surgical chair illustrated in chain lines, by a pair of rods 3 and 4 which are connected to a crossbar 5 via intermediate pieces 6 and 7. The crossbar 5 supports a carrier 8, which may be rotated about the axis of the crossbar 5 and also may be laterally displaced along the axis of the crossbar 5. The carrier 8 is pivotally connected to an additional carrier 9 and forms part of the means for supporting a ring-like curved element 10, which, as illustrated in FIG. 2, is a circular ring with a partial portion of its circumference removed to provide the ring with an opening. As illustrated the ring-like curved element 10 has a radius of curvature which is sufficient to enable the head 11 of the patient to be received therein with a sufficient clearance.

To hold the head 11 in the ring-like curved element 10, a pair of pads 12 are pivotally mounted on an end of a rod 30 (FIG. 2) which, in turn, is mounted on the ring by means 31 for mounting. In a similar manner, a rod or pin 13 having a point or tip 25 is mounted on the ring-like curved element 10 by means 32 for mounting. By turning of the knobs such as 12a and 13a, the rod 30 and the pin or rod 13 can be axially displaced relative to the element 10 so that the point or tip 25 can be screwed a certain distance into the skull 11 and hold the head against the pads 12.

The means for supporting the curved element 10 includes a ball and socket joint 15, which is illustrated in FIGS. 2 and 3 and includes a housing 22 (FIG. 3) mounted on the additional arm 9. The housing 22 receives a ball 15a which has an extension 16. The position of the ball in the housing 22 can be arrested or locked in any given position my manual actuation of a knob 14, which urges a clamping piece 23 to clamp the ball 15a between the piece 23 and a ring-like element 34 which was threaded on the end of the housing 22. Thus, the curved element 10 can be rotated on the axis of the extension 16 and can be displaced or swung in a conical arc.

The extension 16 extends to means 18 for clamping the ring 10 which means 18 is also part of the means for supporting. As illustrated in FIG. 3, the means 18 for clamping includes a clamping block 24 which is urged into clamping engagement on the element 10 by rotation of the knob 17. Thus, the means 18 for clamping can clamp the curved element 10 anywhere along its circumference so that the position of the gap or opening of the element can be changed from the position illustrated in FIG. 2 to enable access to any portion of the head of the patient held in the element 10.

As mentioned hereinabove, the rod 13 as well as the rod 30 are each mounted on the ring-like curved element 10. The curved element 10 is best illustrated in FIG. 2 has a plurality of apertures 19, which are circumferentially spaced therealong with the apertures extending parallel to the axis of the curved element. Each of the mounting means 31 and 32 includes a bolt 20, which has an axis 21 and is received in one of the selected apertures so that the position of the mouting means 31 and 32 on the curved elements 10 can be adjusted. Each of the mounting means 31 and 32 is provided with a wing nut such as 31a and 32a which enables clamping the mounting means in a fixed axial position on its respective bolt 20. Thus, by loosening one of the wing nuts such as 31a or 32a, the respective mounting means can be rotated on the axis 21 of its bolt 20 so that the respective rods such as 30 or 13 extends in the desired direction from the mounting means.

The advantage of these mounting means are that the curved element 10 can be located relative to the head 11 of the patient so that the area of the person's head on which the operation is being performed will be located in the opening of the curved element 10. If a portion of the ring element 10 lies in front of the respiratory passages of the head 11, the head can be located within the curved element 10 in an offset manner so that access to the respiratory passages of the patient by the anesthetist can occur. As illustrated in FIG. 2, it is noted that the center of the head 11 is offset from the center of the element 10.

Thus, the device of the present invention enables positioning the curved element 10 relative to the patient's head by either rotating it on the axis of the extension 16 or swiveling it in the ball and socket joint 15. Also, the opening in the ring-like curved element 10 can be adjusted to a desired area of the head or skull of the patient. The device has been discussed using one set of pads on a rod and one pin, an additional pad or pin can be utilized by providing an additional mounting means such as 31 or 32.

Although various minor modifications may be suggested by those versed in the art, it should be understood that we wish to embody within the scope of the patent warranted hereon, all such modifications as reasonably and properly come within the scope of our contribution to the art.

We claim:

1. A device for holding a head of a patient in a fixed position during a surgical operation comprising a base support, a ring-like curved element having a sufficient radius of curvature to enable receiving the head of the patient within the element, means for supporting the ring-like curved element on the base support including a ball and socket joint having means for manually arresting the joint in any desired postion, a pad supported on a rod acting as a headrest, a pin support on a rod for holding a head in a fixed position on said pad, means for mounting the rod supporting said pad on the element and means for mounting the rod supporting the pin on the element, both of said means for mounting being adjustable to enable changing the length of the respective rods extending from the element to clamp the head of the patient between the pad and pin.

2. A device according to claim 1, wherein the means for supporting includes means for clamping the curved element, said means for clamping being attached to the ball and socket joint by an extension and being manually actuated so that the curved element can be displaced along its circumference in the means for clamping.

3. A device according to claim 1, wherein the curved element is provided with a plurality of spaced apertures with each aperture extending parallel to the axis of curvature of the element, wherein each of the means for mounting includes a bolt extending into a selected one of the apertures so that the positions of the pad and pin can be relatively adjusted along the circumference of the curved element.

4. A device according to claim 3, wherein each of the means for mounting is adjustably positioned on the axis of its bolt so that the rod for the pads and the rod for the pin can extend from the curved element along any line from the axis of the bolt.

5. A device according to claim 3, wherein the means for supporting includes means for clamping the curved element, said means for clamping being attached to the ball and socket joint by an extension and being manually actuated so that the curved element can be displaced along its circumference in the means for clamping.

6. A device according to claim 1, wherein the curved element is a ring-shaped member having an opening in the circumference thereof.

7. A device according to claim 6, wherein the means for supporting includes means for clamping the curved element, said means for clamping being attached to the ball and socket joint by an extension and being manually actuated so that the curved element can be displaced along its circumference in the means for clamping.

8. A device according to claim 6, wherein the curved element is provided with a plurality of spaced apertures with each aperture extending parallel to the axis of curvature of the curved element, and wherein each of the means for mounting includes a bolt extending into a selected one of the apertures so that each of the mounting means for the pad and pin can be selectively adjusted along the circumference of the curved element.

9. A device according to claim 8, wherein each of the means for mounting enables rotation about the axis of the bolt received in the aperture so that the rod for the pad and the rod for the pin can be adjusted to extend from the curved element in any direction.

10. A device according to claim 8, wherein the means for supporting includes means for clamping the curved element, said means for clamping being attached to the ball and socket joint by an extension and being manually actuated so that the curved element can be displaced along its circumference in the means for clamping.

* * * * *